(12) United States Patent
Aamir et al.

(10) Patent No.: US 11,981,949 B1
(45) Date of Patent: May 14, 2024

(54) JUTE FILTERS TO REDUCE AMMONIA INHIBITION EFFECTS OF CHICKEN MANURE FOR BIOGAS PRODUCTION

(71) Applicant: KING FAISAL UNIVERSITY, Al-Ahsa (SA)

(72) Inventors: Muhammad Aamir, Al-Ahsa (SA); Muhammad Hassan, Islamabad (PK); Shah Fahad Bin Masud, Islamabad (PK)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/508,622

(22) Filed: Nov. 14, 2023

Related U.S. Application Data

(62) Division of application No. 18/212,609, filed on Jun. 21, 2023.

(51) Int. Cl.
*C12P 5/02* (2006.01)
*B01D 53/02* (2006.01)
(Continued)

(52) U.S. Cl.
CPC .............. *C12P 5/023* (2013.01); *B01D 53/02* (2013.01); *C02F 11/04* (2013.01); *C12M 21/04* (2013.01); *C12M 23/36* (2013.01); *C12M 27/02* (2013.01); *C12M 29/04* (2013.01); *C12M 41/40* (2013.01); *C12N 1/20* (2013.01); *B01D 2253/20* (2013.01); *B01D 2253/304* (2013.01); *B01D 2253/306* (2013.01); *B01D 2257/406* (2013.01); *B01D 2258/05* (2013.01); *C02F 2103/20* (2013.01)

(58) Field of Classification Search
CPC ..... C12P 5/023; B01D 53/02; B01D 2253/20; B01D 2253/304; B01D 2253/306; B01D 2257/406; B01D 2258/05; C02F 11/04; C02F 2103/20; C12M 21/04; C12M 23/36; C12M 27/02; C12M 29/04; C12M 41/40; C12N 1/20
USPC ........... 210/603, 903; 435/262, 262.5, 289.1, 435/167; 71/10, 21
See application file for complete search history.

(56) References Cited

U.S. PATENT DOCUMENTS 6,299,774 B1 * 10/2001 Ainsworth ............. C12M 47/20
210/603
7,416,664 B2    8/2008 Bonde
(Continued)

FOREIGN PATENT DOCUMENTS

CN      109517730 A  *  3/2019
DE   102013114786 A1  *  6/2015  ............ C12M 21/04
(Continued)

OTHER PUBLICATIONS

Machine-generated English translation of CN 109517730, generated on Jan. 11, 2024.*
(Continued)

*Primary Examiner* — Fred Prince
(74) *Attorney, Agent, or Firm* — Nath, Goldberg & Meyer; Richard C. Litman

(57) ABSTRACT

A system and method for producing biogas (methane) from a mixture of poultry manure and methanogens through an anaerobic digestion process which makes use of jute filters within the chamber to absorb excess ammonium nitrogen from the mixture of poultry manure.

8 Claims, 2 Drawing Sheets

(51) Int. Cl.
  *C02F 11/04* (2006.01)
  *C12M 1/00* (2006.01)
  *C12M 1/06* (2006.01)
  *C12M 1/107* (2006.01)
  *C12M 1/34* (2006.01)
  *C12N 1/20* (2006.01)
  *C02F 103/20* (2006.01)

(56) References Cited

U.S. PATENT DOCUMENTS

| | | | | |
|---|---|---|---|---|
| 8,580,219 | B2 * | 11/2013 | Hickey | C10K 1/08 |
| | | | | 210/603 |
| 10,029,922 | B2 | 7/2018 | Segroves et al. | |
| 10,850,995 | B2 | 12/2020 | Hasegawa et al. | |
| 2002/0079266 | A1 * | 6/2002 | Ainsworth | C05F 17/40 |
| | | | | 210/603 |
| 2005/0167359 | A1 * | 8/2005 | Wilkie | C02F 3/2806 |
| | | | | 210/603 |
| 2008/0283468 | A1 * | 11/2008 | Logan | C12M 41/12 |
| | | | | 210/603 |
| 2010/0326907 | A1 * | 12/2010 | Gavrieli | B01D 29/01 |
| | | | | 210/615 |
| 2012/0312742 | A1 * | 12/2012 | Sassow | C02F 11/04 |
| | | | | 210/603 |
| 2014/0377929 | A1 | 12/2014 | Jarvinen et al. | |
| 2015/0060356 | A1 * | 3/2015 | Barry | C02F 3/28 |
| | | | | 210/603 |

FOREIGN PATENT DOCUMENTS

| | | | | |
|---|---|---|---|---|
| RO | 122198 B1 | 2/2009 | | |
| WO | WO-2007003689 A1 * | 1/2007 | | B01D 53/02 |
| WO | WO-2011112737 A2 * | 9/2011 | | C02F 3/006 |
| WO | 2021161337 A1 | 8/2021 | | |

OTHER PUBLICATIONS

Machine-generated English translation of DE 102013114786, generated on Jan. 11, 2024.*

Samadi, M. T. et al., "Anaerobic co-digeston using poultry slaughterhouse and vegetable wastes to enhance biogas yield: effect of different C/N ratios", Biomass Conversion and Biorefinery (2022). https://doi.org/10.1007/s13399-022-03501-1.

* cited by examiner

JUTE FILTERS TO REDUCE AMMONIA INHIBITION EFFECTS OF CHICKEN MANURE FOR BIOGAS PRODUCTION

CROSS-REFERENCE TO RELATED APPLICATION

This application is a divisional of U.S. patent application Ser. No. 18/212,609, filed on Jun. 21, 2023, the entire contents of which are incorporated herein by reference.

BACKGROUND

1. Field

The present disclosure relates to a bioreactor. More specifically it relates to an anaerobic digester (AD) for production of biogas from animal waste.

2. Description of the Related Art

Globally, urbanization, industrialization, and economic growth have resulted in increased waste generation per person. It is also a fact that as the world population continues to grow together with the progress of human civilization, the global demand for energy increases. Traditional energy sources such as fossil fuels including coal, petroleum, natural gas, etc., are being exhausted at an accelerating pace. Nuclear and thermal power pose potential risks to the environment and public health. And solar and wind power, while cleaner, can only address the problem marginally.

Finding new ways to obtain energy from biodegradable waste might help solve these problems. For example, biodegradable waste can be converted to biogas using an anaerobic digestion (AD) system. This would be beneficial for human health, help preserve the environment, stimulate the economy, and conserve energy. As such, AD systems have attracted remarkable attention in the scientific community. However, the lack of an appropriate bioreactor to handle the biodegradable waste is a major drawback in most AD systems, as the currently available AD systems are mainly developed for handling low-solid feedstocks, such as agricultural and industrial wastewater, livestock manure, waste activated sludge, food waste, etc. Continuously stirred tank reactors (CSTR) and up-flow anaerobic sludge blanket (UASB) reactors have been the most common types of ADs applied in industrial scale biogas plants for treating high moisture organic waste in recent decades.

Nevertheless, there are inherent deficiencies associated with the abovementioned reactor types. One problem that occurs using CSTRs is the formation of floating layers, which makes stirring difficult, thus inhibiting the formation of biogas. Other disadvantages of the CSTR reactors are low conversion per unit volume and poor agitation. As for UASB systems, the complexity in control of operation and process parameters for a two stage leach bed-UASB reactor makes it less practical for industry. Other challenges inherent to a standard AD system are related to relatively low methane yield, slow methane generation, and potential process instability.

When low-solid feedstocks of livestock or poultry manure are used for biogas production, the higher nitrogen content of poultry manure leads to a carbon to nitrogen (C:N) ratio of (8-12). However, for optimum biogas production, the C/N ratio should be in the range of (20-30). If the C/N ratio of the substrate used is lower, optimum biogas production is severely impeded due to the accumulation of nitrogen. Methanogens are the main bacteria responsible for consuming the solid waste of poultry manure and producing methane gas for fuel. However, the use of poultry manure in CSTR reactors in commercial biogas plants has not been widely adopted do to the undesirable high nitrogen levels associated with the poultry manure. Currently, when nitrogen levels are not monitored and run unchecked, biogas plant production suffers due to the inefficiency associated with the methanogens being unable to process the poultry manure. As a result, the CSTR reactors become choked and have to be shut down for time consuming and costly maintenance.

What is needed is a method and device for ensuring that nitrogen levels in CSTRs which generate methane gas for biogas production from poultry manure are monitored and alleviated so that the anaerobic digestion driven by the methanogens can continue unimpeded allowing the biogas plant production to continue without significant downtime of the CSTRs.

SUMMARY

The present subject matter is directed towards a method and device of biogas production from animal waste such as poultry manure.

In one embodiment, the present subject matter relates to a device for converting animal waste to biogas, comprising: an inlet for inputting a feed stream of animal waste and a cell culture; a shell/digester tank for receiving said feed stream of said animal waste and said cell culture and facilitating an anaerobic digestion of the animal waste by the cell culture to produce a biogas and ammonium nitrogen; a first outlet for outputting said biogas; one or more jute filters situated within said shell/digester tank for absorbing the ammonium nitrogen produced by said anaerobic digestion; a roof plate mounted on a top of the shell/digester tank; a bottom plate affixed to a bottom of the shell/digester tank, wherein said roof plate, said shell/digester tank, and said bottom plate form an interior volume of a semi-continuous stirring tank reactor (CSTR); and a central shaft agitator located within an interior space of said shell/digester tank for continuously stirring the feed stream of said animal waste.

In this regard, the present device can comprise a bioreactor provided for production of biogas, wherein the bioreactor comprises a shell/digester tank with a roof plate and a bottom plate, wherein the shell digester comprises one or more inlets for a feed stream of poultry manure and cell cultures of methanogens and one or more outlets for biogas exit, recycling of cell cultures of methanogens and/or the transfer of partially digested waste to another tank for drainage purposes of the digester tank. The shell/digester tank can comprise a central agitator shaft, wherein the central agitator shaft is connected to a drive motor on top of the roof plate through an agitator entry hole in the roof plate and extends vertically downward towards the bottom plate. The central agitator shaft can have an array of stirrers extending radially outward from the central agitator shaft at fixed vertical increments along the height of the central agitator shaft. One or more jute filters are attached to an inner circumferential surface of the shell/digester tank to absorb ammonium nitrogen from the digestion process.

In another embodiment, the present subject matter relates to a method for using a semi-continuous stirring tank reactor (CSTR) for converting animal waste to biogas, comprising: making a slurry comprising animal waste and a cell culture; inputting, thorough an inlet, a feed stream of said slurry of animal waste and cell culture into an interior volume of a shell/digester tank; receiving, at an interior volume of said shell/digester tank, said slurry of said animal waste and said cell culture and facilitating an anaerobic digestion of the animal waste by the cell culture to produce a biogas and ammonium nitrogen; outputting, by a first outlet, said biogas; absorbing, by one or more jute filters situated within said shell/digester tank, the ammonium nitrogen produced by said anaerobic digestion; and continuously stirring, using a central shaft agitator located within the interior volume of said shell/digester tank, the slurry of said animal waste and the cell culture.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF EMBODIMENTS

Figure 1:
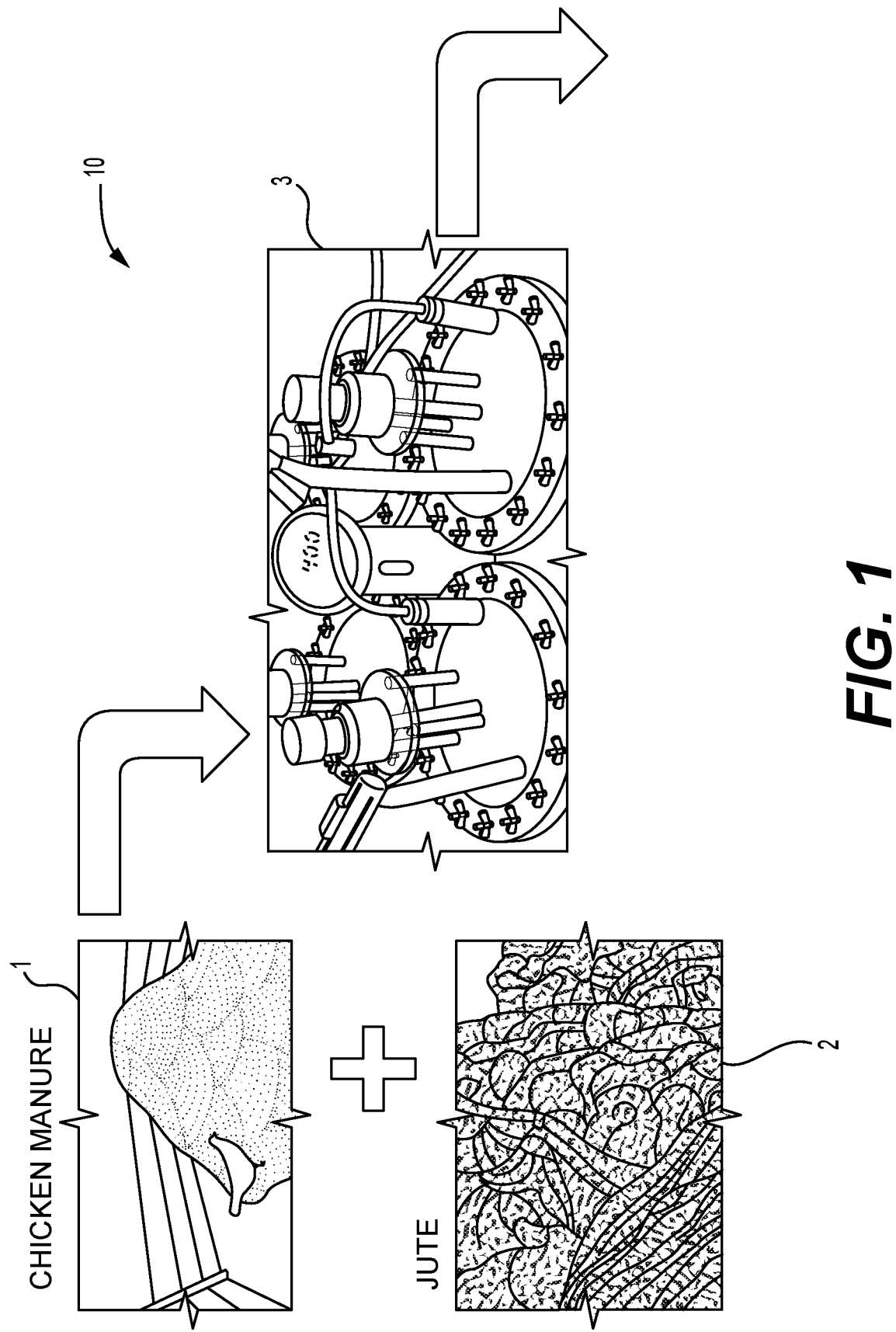
FIG. 1 is a flow diagram of the present methods.

The following detailed description is merely exemplary in nature and is not intended to limit the described embodiments or the application and uses of the described embodiments. Any implementation described herein with the words "exemplary" or "illustrative" is not necessarily construed as preferred or advantageous over other implementations. All of the implementations described below are exemplary implementations provided to enable persons skilled in the art to make or use the embodiments of the disclosure and are not intended to limit the scope of the disclosure, which is defined by the claims. For the purposes of the description herein, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed therein are not to be considered as limiting, unless the claims expressly state otherwise.

In one embodiment, the present subject matter relates to a device for converting animal waste to biogas, comprising: an inlet for inputting a feed stream of animal waste and a cell culture; a shell/digester tank for receiving said feed stream of said animal waste and said cell culture and facilitating an anaerobic digestion of the animal waste by the cell culture to produce a biogas and ammonium nitrogen; a first outlet for outputting said biogas; one or more jute filters situated within said shell/digester tank for absorbing the ammonium nitrogen produced by said anaerobic digestion; a roof plate mounted on a top of the shell/digester tank; a bottom plate affixed to a bottom of the shell/digester tank, wherein said roof plate, said shell/digester tank, and said bottom plate form an interior volume of a semi-continuous stirring tank reactor (CSTR); and a central shaft agitator located within an interior space of said shell/digester tank for continuously stirring the feed stream of said animal waste.

In this regard, the animal waste to be converted can be poultry manure. Further, the cell culture can comprise methanogens, and the produced biogas can be methane.

In an embodiment, the central shaft agitator can extend vertically downwards towards the bottom plate. In this regard, the central shaft agitator can further comprise an array of stirrers situated at vertical increments along a length of said central shaft agitator. The central shaft agitator can be coupled to a motor, which can cause the central shaft agitator to rotate about a central axis. In an embodiment, the motor coupled to the central shaft agitator can cause the central shaft agitator to rotate about a central axis continuously stirring the interior volume of said semi-continuous stirring tank reactor at a speed of about 1 rpm to about 100 rpm. The motor can be mounted atop said roof plate and can connect to a first end of the central agitator shaft.

In another embodiment, the one or more jute filters can be located all along a surface of an inner circumference of the cylinder of the shell/digester tank. In this regard, the one or more jute filters can comprise one or more jute sheets, each having a thickness of about 2 cm, 2 cm, or about 1 to about 3 cm. Similarly, the one or more jute sheets can each have a surface area of about 100 $cm^2$, at least about 100 $cm^2$, or about 90 $cm^2$ to about 110 $cm^2$. Further, the one or more jute filters can comprise one, two, three, four, or more such jute sheets located along the surface of the inner circumference of the shell/digester tank. In an embodiment, four jute sheets are located along the surface of the inner circumference of the shell/digester tank.

In an embodiment, the interior volume of said semi-continuous stirring tank reactor is about 10 liters. In certain embodiments, the shell/digester tank can be in a shape of a cylinder. In another embodiment, said shell/digester tank can further include a pressure gauge for controlling a pressure of the interior volume of the semi-continuous stirring tank reactor.

In another embodiment, the present subject matter relates to a method for using a semi-continuous stirring tank reactor (CSTR) for converting animal waste to biogas, comprising: making a slurry comprising animal waste and a cell culture; inputting, thorough an inlet, a feed stream of said slurry of animal waste and cell culture into an interior volume of a shell/digester tank; receiving, at an interior volume of said shell/digester tank, said slurry of said animal waste and said cell culture and facilitating an anaerobic digestion of the animal waste by the cell culture to produce a biogas and ammonium nitrogen; outputting, by a first outlet, said biogas; absorbing, by one or more jute filters situated within said shell/digester tank, the ammonium nitrogen produced by said anaerobic digestion; and continuously stirring, using a central shaft agitator located within the interior volume of said shell/digester tank, the slurry of said animal waste and the cell culture.

In this regard, the animal waste used in the present methods is poultry manure and the produced biogas is methane. The poultry manure can be fed into the shell/digester tank continuously for 10, 20, 30, 40, 50, 60, 70 80, 90, or more days, or for 80 days. Further, the one or more jute filters can reduce the content of ammonium nitrogen in the shell/digester tank by at least about 68% and increase methane production by at least about 72%.

Figure 2:
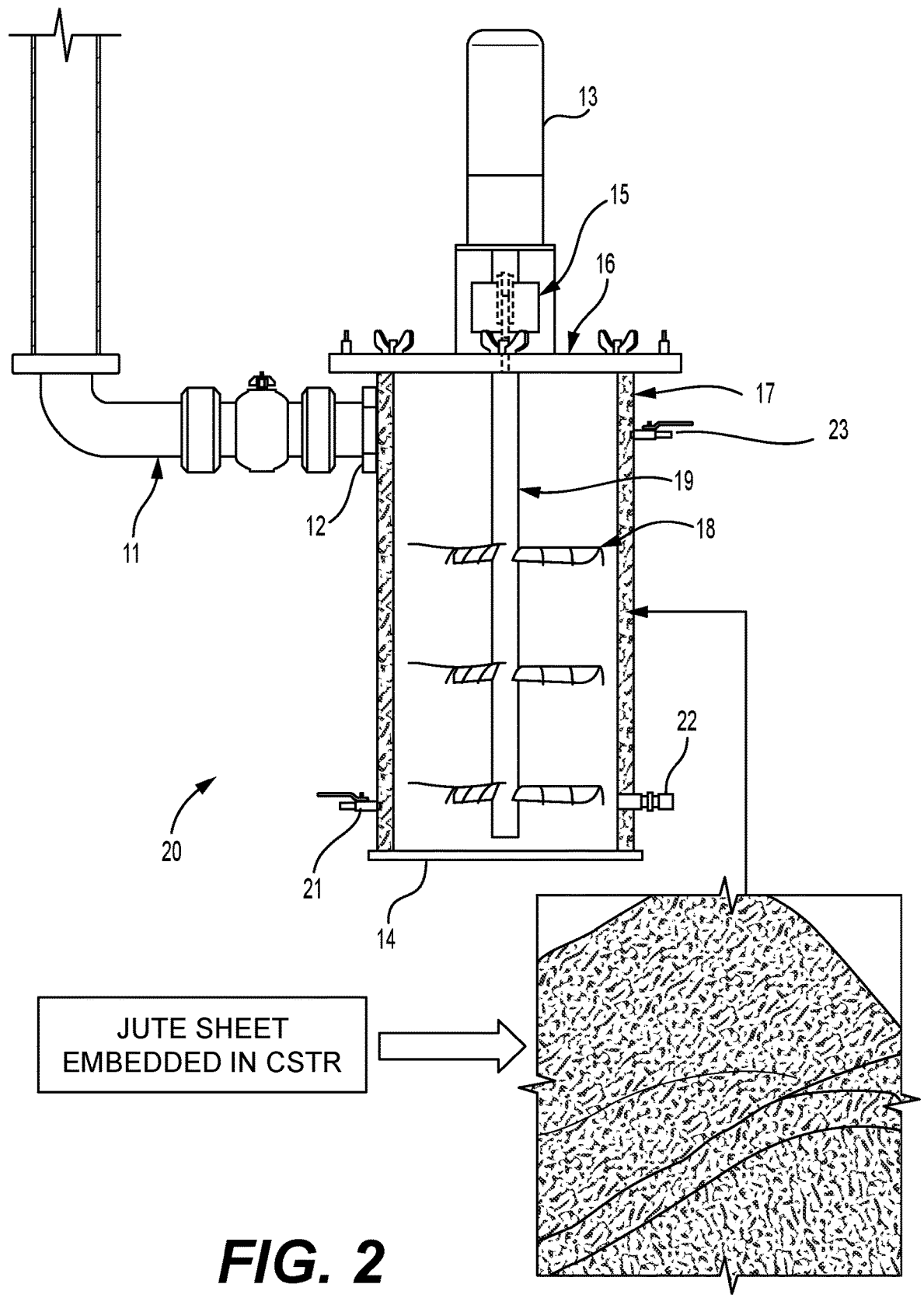
FIG. 2 is a diagram of a semi-continuous stirring tank reactor (CSTR).

FIG. 2 shows a detailed depiction of a bioreactor (20), in this instance in the form of a semi-continuous stirring tank reactor (CSTR), provided for the production of biogas. The bioreactor comprises a shell/digester tank (17) with a roof plate (16) and a bottom plate (14). The shell/digester tank (17) comprises one or more inlets (11) for a feed stream of a slurry of poultry manure and cell cultures of methanogens which connects to the shell/digester tank (17) near a top entry point (12) just below where the roof plate (16) extends out over the top of the shell/digester tank (17). The water jacket to keep the CSTR warm at 37° C. has an outlet (21). In addition, the bioreactor has a biogas collection nozzle outlet (23) installed at the top of the CSTR and one outlet for recycling of cell cultures of methanogens and/or the transfer of partially digested waste to another tank for drainage purposes of the digester tank (22). The bioreactor also comprises a central agitator shaft (19), wherein the central agitator shaft (19) is connected to a drive motor (13) at the top of the shell/digester tank (17) through an agitator entry hole in the roof plate (16) wherein the central agitator shaft (19) extends downward towards the bottom plate (14). Also included, but not shown is a pressure gauge attached to the shell/digester tank (17) wherein the pressure gauge is used to measure the pressure of the shell/digester tank (17).

At least one jute filter is embedded in the shell/digester tank (17) (FIG. 2, see inset) and is attached along an inner circumferential surface of the shell/digester tank (17). The central agitator shaft (19) has an array of stirrers (18) extending radially outward from the central agitator shaft at fixed vertical increments along the height of the central agitator shaft (19). The central agitator shaft (19) attaches to the motor (13) at a point external to the shell/digester tank (17) in a housing (15) situated atop the roof plate (16) such that misalignment of the central agitator shaft (19) with the motor (13) can be monitored and corrected when the need arises.

In an embodiment, the at least one jute filter is constructed from one, two three or four pieces of jute sheets. In this regard, each jute sheet can be about 2 cm thick, 2 cm thick, or about 1 to about 3 cm thick, and can have a surface area of 100 cm$^2$. The jute sheets can be installed in the shell/digester tank (17) to efficiently process a working volume of 10 liters within the shell/digester tank (17). In an embodiment, the jute filters/sheets are removable from the shell/digester tank (17) and can be replaced with fresh, clean jute filters/sheets to allow the bioreactor to continue in operation. In certain embodiments, the jute filters/sheets can be removed from the shell/digester tank (17) on or about the 30$^{th}$, 45$^{th}$, and 80$^{th}$ days of operation. Once removed, the jute filter/sheets can be cleaned, thereby permitting the jute filters/sheets to be then re-inserted into the shell/digester tank (17) for further use. This cleaning process can enhance the ammonia removal efficiency of the jute filters/sheets, and permits them to be recycled, in use.

The motor (13) can cause the central agitator shaft (19) to rotate about a central axis at a speed of 1 rpm to 100 rpm, thereby continuously stirring the slurry contained within the shell/digester tank (17) depending on the speed requirements needed to maintain a uniform viscosity of the slurry, to maintain uniform cell density, and to provide an even cell distribution.

The shell/digester tank (17) may be made of materials compatible to the anaerobic treatment of waste(s) including but not limited to steel, fiber reinforced polymers, plastic, concrete, and any combinations thereof. The central agitator shaft may be made of materials compatible to the anaerobic treatment of waste(s) including but not limited to steel, fiber, reinforced polymers, plastic, and any combinations thereof. Likewise, although the shape of the shell/digester tank (11) is shown as a cylinder, the shape is not limited to such a configuration and can accommodate various other shapes such as rectangular, square, etc.

In an experiment, the slurry of poultry manure and cell culture was fed into a test CSTR for 80 days while a control CSTR was operated in a similar fashion, but without the installation of jute filters, in order to compare results. The jute filters in the test CSTR acted as efficient sponges and absorbed accumulated nitrogen in the shell/digester tank (17) such that there was a 68% reduction in ammonium nitrogen, which led to a 72% increase in methane generation when compared with the control CSTR. Also, no choking of the test CSTR was observed during the test run period. The jute filters were expelled from the test CSTR shell/digester tank (17) on the 30$^{th}$, 45$^{th}$, and 80$^{th}$ day of the experiments and cleaned to enhance the ammonia removal efficiency of the filters.

As shown in FIG. 1, a method for biogas generation includes a method for the production of biogas using the bioreactor comprising the steps of: making a slurry comprising poultry waste (1) and a cell culture of methanogens; feeding the slurry into said bioreactor (3); carrying out an anaerobic digestion process in the bioreactor at a controlled condition to produce biogas (FIG. 1, arrow pointing out); and absorbing excess nitrogen generated in the anaerobic digestion process onto a jute filter (2).

It is to be understood that method and device for producing a biogas from poultry manure is not limited to the specific embodiments described above but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method for using a semi-continuous stirring tank reactor (CSTR) for converting animal waste to biogas, comprising:
    making a slurry comprising animal waste and a cell culture;
    inputting, thorough an inlet, a feed stream of said slurry of animal waste and cell culture into an interior volume of a shell/digester tank;
    receiving, at an interior volume of said shell/digester tank, said slurry of said animal waste and said cell culture and facilitating an anaerobic digestion of the animal waste by the cell culture to produce a biogas and ammonium nitrogen;
    outputting, by a first outlet, said biogas;
    absorbing, by one or more jute filters each having a thickness of about 1 to about 3 cm situated within said shell/digester tank, the ammonium nitrogen produced by said anaerobic digestion; and
    continuously stirring, using a central shaft agitator located within the interior volume of said shell/digester tank, the slurry of said animal waste and the cell culture.

2. The method for using the semi-continuous stirring tank reactor for converting animal waste to biogas as recited in claim 1, wherein said animal waste is poultry manure.

3. The method for using the semi-continuous stirring tank reactor for converting animal waste to biogas as recited in claim 1, wherein said biogas is methane.

4. The method for using the semi-continuous stirring tank reactor for converting animal waste to biogas as recited in claim 1, wherein said one or more jute filters reduce the content of ammonium nitrogen in the shell/digester tank by at least about 68% and increase methane production by at least about 72%.

5. The method for using the semi-continuous stirring tank reactor for converting animal waste to biogas as recited in claim 1, wherein said one or more jute filters each have a thickness of about 2 cm.

6. The method for using the semi-continuous stirring tank reactor for converting animal waste to biogas as recited in claim 1, wherein said one or more jute filters each have a surface area of about 90 cm² to about 110 cm².

7. The method for using the semi-continuous stirring tank reactor for converting animal waste to biogas as recited in claim 1, comprising four of the one or more jute filters.

8. The method for using the semi-continuous stirring tank reactor for converting animal waste to biogas as recited in claim 7, wherein the semi-continuous stirring tank reactor has a volume of about 10 liters.

\* \* \* \* \*